United States Patent [19]
Williams et al.

[11] Patent Number: 5,993,657
[45] Date of Patent: Nov. 30, 1999

[54] ADJUSTABLE COLLECTION CANISTER FOR CONTINUOUS RENAL REPLACEMENT THERAPY

[76] Inventors: Edward L. Williams; Holly R. Williams, both of 2417 W. Azalea, Tyler, Tex. 75701

[21] Appl. No.: 09/018,090

[22] Filed: Feb. 3, 1998

[51] Int. Cl.[6] .............................. B01D 35/30; A61M 1/00; F04B 49/00
[52] U.S. Cl. ...................... 210/321.65; 141/21; 210/436; 222/309; 222/444; 604/190; 604/317; 604/318
[58] Field of Search .................................. 210/252, 257.1, 210/257.2, 321.65, 436, 472, 513; 141/21, 55, 192, 291, 292; 604/187, 190, 317, 318, 403, 404, 4; 222/309, 444

[56] References Cited

U.S. PATENT DOCUMENTS

| | | | |
|---|---|---|---|
| 3,680,560 | 8/1972 | Pannier, Jr. et al. | 128/276 |
| 3,768,478 | 10/1973 | Fertik et al. | 128/276 |
| 4,132,644 | 1/1979 | Kolberg | 210/85 |
| 4,204,957 | 5/1980 | Weickhardt | 210/98 |
| 4,253,501 | 3/1981 | Ogle | 141/27 |
| 4,275,732 | 6/1981 | Gereg | 128/276 |
| 4,572,210 | 2/1986 | McKinnon | 604/190 |
| 4,728,433 | 3/1988 | Buck et al. | 210/646 |
| 4,767,399 | 8/1988 | Bollish | 604/5 |
| 4,923,598 | 5/1990 | Schal | 210/87 |
| 5,211,849 | 5/1993 | Kitaevitch et al. | 210/645 |

*Primary Examiner*—John Kim
*Attorney, Agent, or Firm*—C. W. Alworth

[57] ABSTRACT

A waste liquid collection system for use in continuous arteriovenous or venovenous hemodialysis (CAVH or CVVH) is disclosed. The system comprises a collection vessel and associated interconnection lines which can be preset to given volume of waste liquid to be removed from the dialysis machine in a given period of time. Once the volume is reached, the collection vessel stops waste liquid flow until the vessel is emptied and reset. The system guaranties that excess liquid will not be removed from a patient.

13 Claims, 6 Drawing Sheets

ADJUSTABLE COLLECTION CANISTER FOR CONTINUOUS RENAL REPLACEMENT THERAPY

TECHNICAL FIELD OF THE INVENTION

The instant invention relates to dialysis and in particular to continuous renal replacement therapy whereby an apparatus and method for the regulated collection of soluble waste from the dialysis process allows for precise control of volumetric removal.

BACKGROUND OF THE INVENTION

For various reasons, including ill health, injury or surgery, patients may require substitution in the form of replacement or supplementation of the patient's natural kidney function in order to remove waste liquids from the patient's system. Such liquids would include excess liquids (due to the regulated addition of prescribed liquid or other liquids required to sustain the patient) and liquids containing dissolved waste products entrained in the patient's blood. There are several procedures used for the above purpose and include, hemodialysis, hemofiltration, and ultrafilation. All of these procedures result in the removal of waste products from the patient. Essentially the patent's blood is passed through a filter or membrane from which the waste liquid is removed and the blood is passed back into the patient. The replacement or augmentation of the patient's natural renal function can affect the balance of the body chemistry. In particular, the removal of waste liquids must be carefully controlled.

One of the procedures used for critically ill or injured patients is continuous arteriovenous or venovenous hemodialysis (CAVH or CVVH—in general CRRT, continuous renal replacement therapy). In these procedures the patient is on dialysis twenty-four hours per day, seven days per week for extended periods of time. CRRT is similar to hemodialysis, except that the patient is on the machine (the filter system) continuously rather than for several hours at varying increments of time. In CRRT, it is important to keep accurate records of dialysis liquids and intravenous liquids entering the patient and the amount of liquids leaving the patient. That is, a mass balance must exist when drawn about the patient. Severe clinical problems, and even death, may occur if these fluid balances are not carefully regulated.

Therefore, it is critical in CRRT to monitor, regulate and control the rate and volume of liquid removal from the patient.

PRIOR ART

There are two simple methods used to collect the waste liquid coming from the patient undergoing CRRT. The first is an electric metering pump whose flow rate may be set by an operator. The operator would set the volumetric rate of the metering pump equal to the amount prescribed to be removed from the patient. Such a system is disclosed by Bollish in U.S. Pat. No. 4,767,399 which uses a volumetric pump. The second simple method utilizes a standard urine collection bag hung on an intravenous pole. The input tube of the bag is coupled to the waste output of hemofilter. The rate of collection of waste liquid is regulated by raising or lowering the height of the urine (collection) bag. Both of these simple methods utilize the natural body pressure of the patient (hydrostatic) to operate in conjunction with the hemofilter and drive waste liquids through the filter and to the collection apparatus, be it a pump or a urine bag.

The first method is by far the best; however, due to the critical nature of these pumps, they are rather expensive. The second is the least expensive and is used extensively because of economic considerations and the fact that there are no other options; however, it does not have the precision of the first method.

The collection bag method is very inaccurate for several reasons. First, a urine bag is not properly graduated as to the quantity of entrained liquid. Second, it is extremely difficult to regulate the rate of collection of waste liquid. Third, as the level of waste liquid increases, the back pressure increases and the rate of collection falls off. Fourth, very often the patient's liquid status (blood pressure) is so high that raising the urine collection bag (to regulate liquid removal) places the bag at the ceiling level making precise regulation almost impossible, Thus, it is very difficult to regulate the liquid removal (collection) rate to exact standards on a per hour basis and, more often than not, either too much liquid or not enough liquid is removed on a per hour basis. Any differences between the rate of liquid infusion and the rate of liquid removal must be adjusted during the subsequent periods.

A third method, combining rate of liquid infusion with rate of liquid removal, involves a complex and expensive dialysis apparatus. Such systems are disclosed by Weickhardt (U.S. Pat. No. 4,204,957), Kolberg (U.S. Pat. No. 4,132,644), Buck et al. (U.S. Pat. No. 4,728,433), and Kitaevich et al. (U.S. Pat. No. 5,211,849) all of which use a weighing scheme to set the rate of removal of waste liquid equal to the rate of liquid infusion. Schäl (U.S. Pat. No. 4,923,598) discloses a complex dialysis apparatus that uses highly accurate flow meters to measure the rate of liquid infusion and removal. These systems are extremely expensive and are not found in many hospitals.

The Bollish system, modifications to it, and the simple self pressurizing system which takes advantage of body liquid pressure to expunge waste products from the hemofilter and into a collection bag, are the most common systems. The self pressurizing system appears to be very common but suffers from poor regulation of the rate of removal of the waste liquid.

Thus, there remains a need for a waste liquid collection system that can reliably operate in conjunction with the self pressurizing hemofilter dialysis system; that can be easily regulated; that has a built in safety function which will stop liquid removal, if the per hour volumetric removal rate is exceeded; that is inexpensive; that is easy to use; and that is mechanically stable.

SUMMARY OF THE INVENTION

The present invention is designed to resolve all the problems associated with the urine bag collection method used in conjunction with a self pressurizing hemofilter, while retaining the cost advantage of the urine bag. It may be used with a variety of dialysis systems (or apparatuses) as the collection vessel providing an overall safety shutoff.

The collection system of the instant invention comprises of a collection canister, an internal hydrophobic membrane, a three-way stop cock, a liquid regulating clamp, and the necessary medical hoses required to attach the canister to the hemofilter and to a proper waste liquid disposal point. The canister can be made from a three-liter syringe with a modified plunger. Three-liter syringes are available with precise graduations on the wall of the syringe and with a flat bottom and a single port located in the base of the syringe. In the prototype, the plunger was modified so that air could readily pass through the plunger.

The plunger modification can be made in several ways. For example, in the first prototype a single hole was drilled in the plunger and plugged with a 0.2 micron hydrophobic membrane. (It would be easier to manufacture the plunger with a plurality of pass holes.) The net effect is that air can pass through the plunger, but any liquid will be "shut-off" by the hydrophobic membrane. In other words, the plunger will pass air and not act as a plunger; however, it will not pass liquids and will act as a plunger whenever the canister is completely filled with liquid.

The three-way stop cock or three-way valve allows liquid flow from the hemofilter into the canister, and it may block such flow whenever necessary. The three-way valve will also allow flow from the canister to an approved disposal point; thus, allowing the canister to be emptied once it is full. During the emptying cycle the hemofilter will be isolated from the canister. Thus, the three-way valve has a minimum of two positions, flow from the hemofilter to the canister (fill), and flow from the canister to an approved drain point (drain). The three-way valve will NOT allow direct flow from the hemofilter to the drain. Some three-way valves incorporate a third position, all flow blocked (stop).

The apparatus is placed in service by connecting the canister to the hemofilter outlet. This will allow the outlet (waste) liquids to pass from the filter, through the three-way stop cock and into the canister. The other line coming from the three-way cock is taken to an approved waste liquids disposal point. The disposal point should be level with or preferably below the grade of the bottom of the collection canister of the instant invention. A roller clamp, or similar adjustable constricting clamp is placed on the line coming from the hemofilter to the three-way stop cock. Finally, the plunger is set at the volume of liquid which is to be removed during the removal period. (The removal period is generally one hour and will be set by the prescribing physician.)

The three-way stop cock should be positioned to allow liquid to flow from the hemofilter to the canister. The rate of liquid removal should be monitored, and the roller clamp adjusted to obtain the required removal rate. This adjustment will have to made by trial and error while watching and timing the increase of liquid level in the canister. If the adjustment is made properly, the liquid level in the canister will reach the plunger at the end of the removal period. While the canister is filling, air entrained within the canister can pass through the hydrophobic filter; however, as soon as the liquid comes in contact with the filter, no liquid can pass through the filter and the canister "shuts-off" the removal of waste liquid. Thus, the canister cannot accept any more liquid and acts as a volume limiter or safety shut off system.

At the end of the removal period, the three-way stop cock is moved to the drain position; thus, stopping flow from the hemofilter and allowing drainage of the removed liquid to the disposal point. Emptying the canister will take about one to two minutes. Once the canister is emptied, the three-way stop cock is moved to the fill position and the cycle starts all over again. It may be necessary to adjust the roller clamp to obtain the proper removal rate. The plunger can be adjusted at prescribed intervals to alter the volume of liquid removal.

DESCRIPTION OF THE PREFERRED EMBODIMENT

Figure 1:
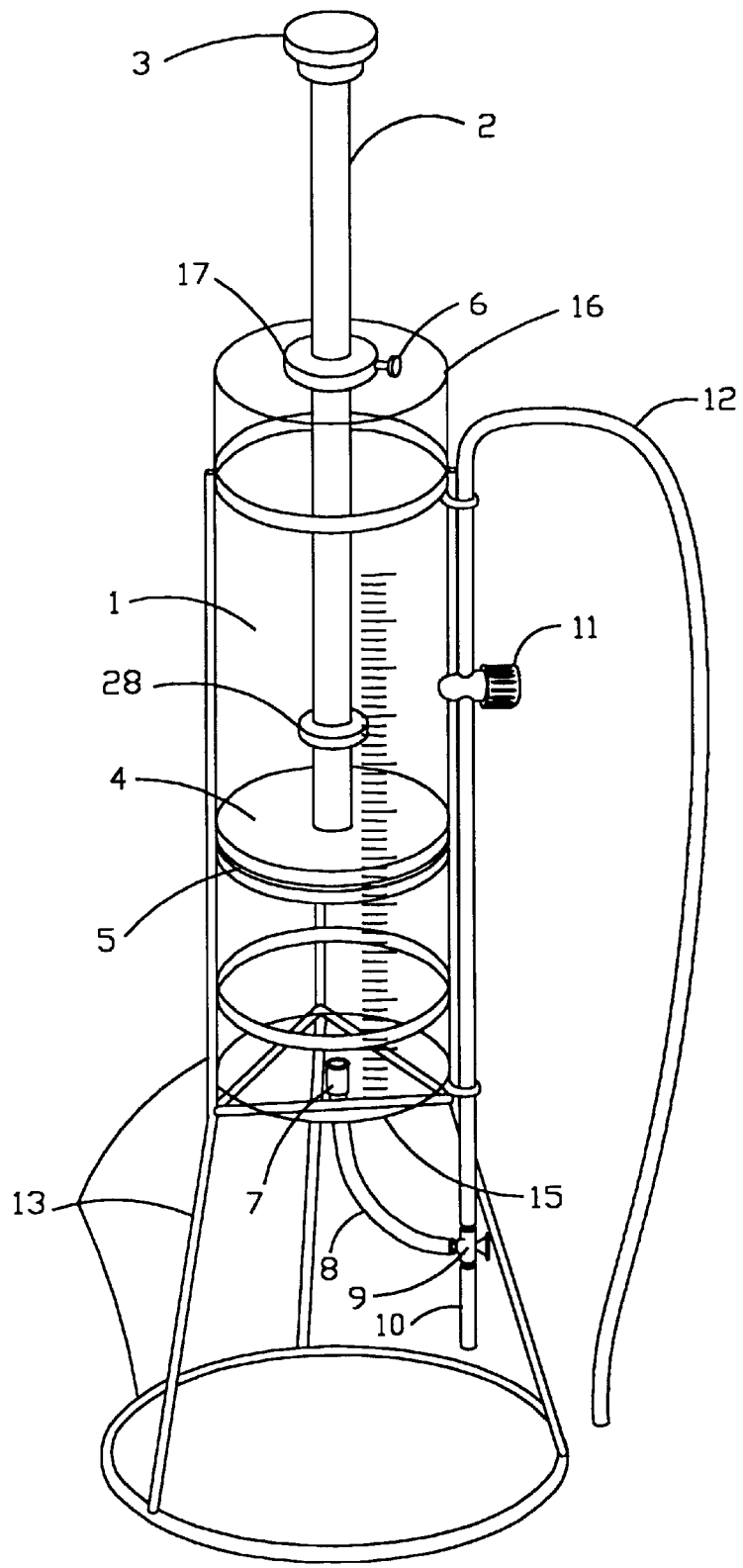
FIG. 1 shows a prototype collection system including inlet and outlet lines, a roller clamp used as a restrictor and the three-way stop cock.
Figure 2:
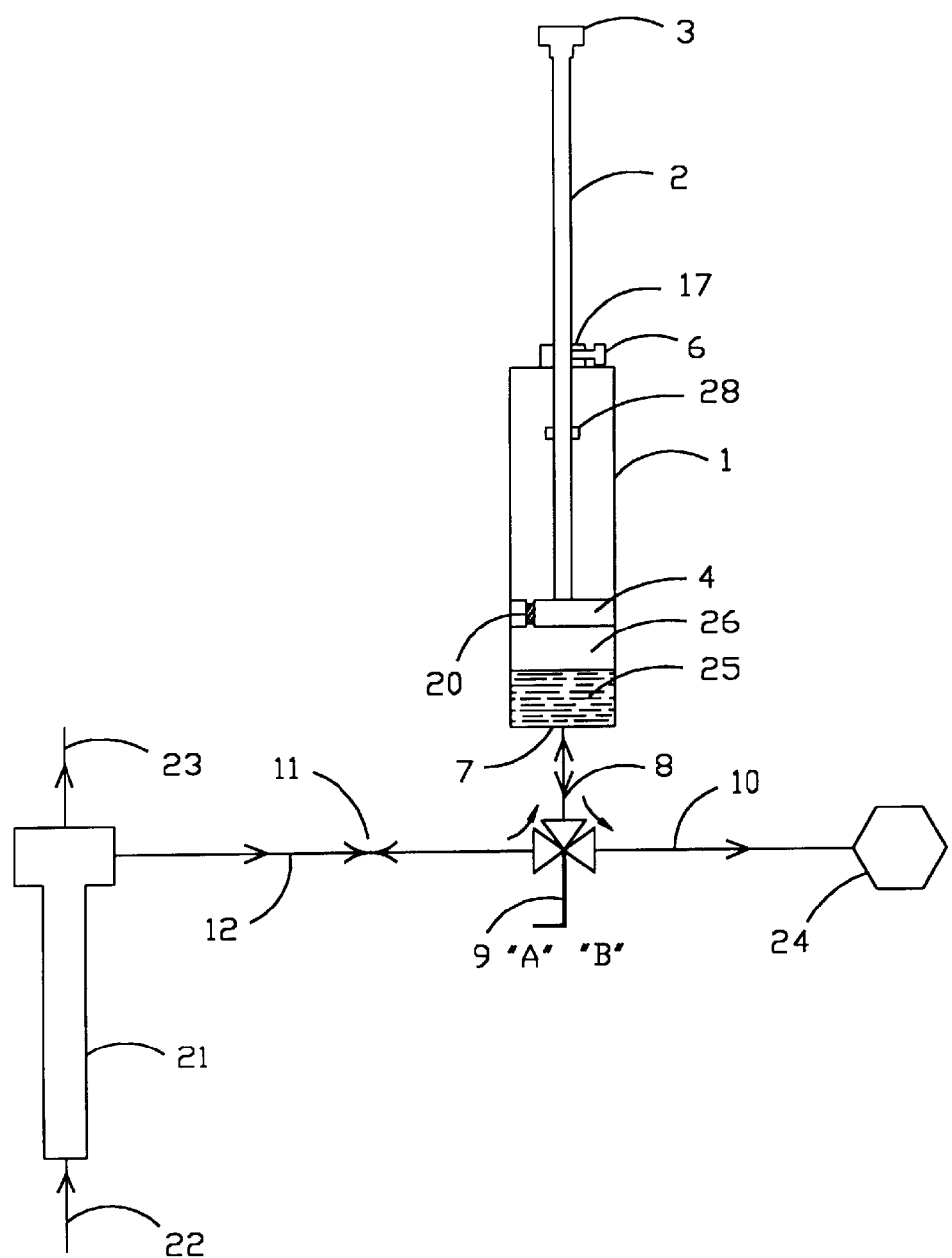
FIG. 2 is a schematic representation of the collection apparatus showing the hemofilter, the line leading from the filter to the three-way stop cock, the associated flow restrictor device, the three-way stop cock, the collection canister, and the line leading from the three-way stop cock to the proper disposal point.
Figure 3:
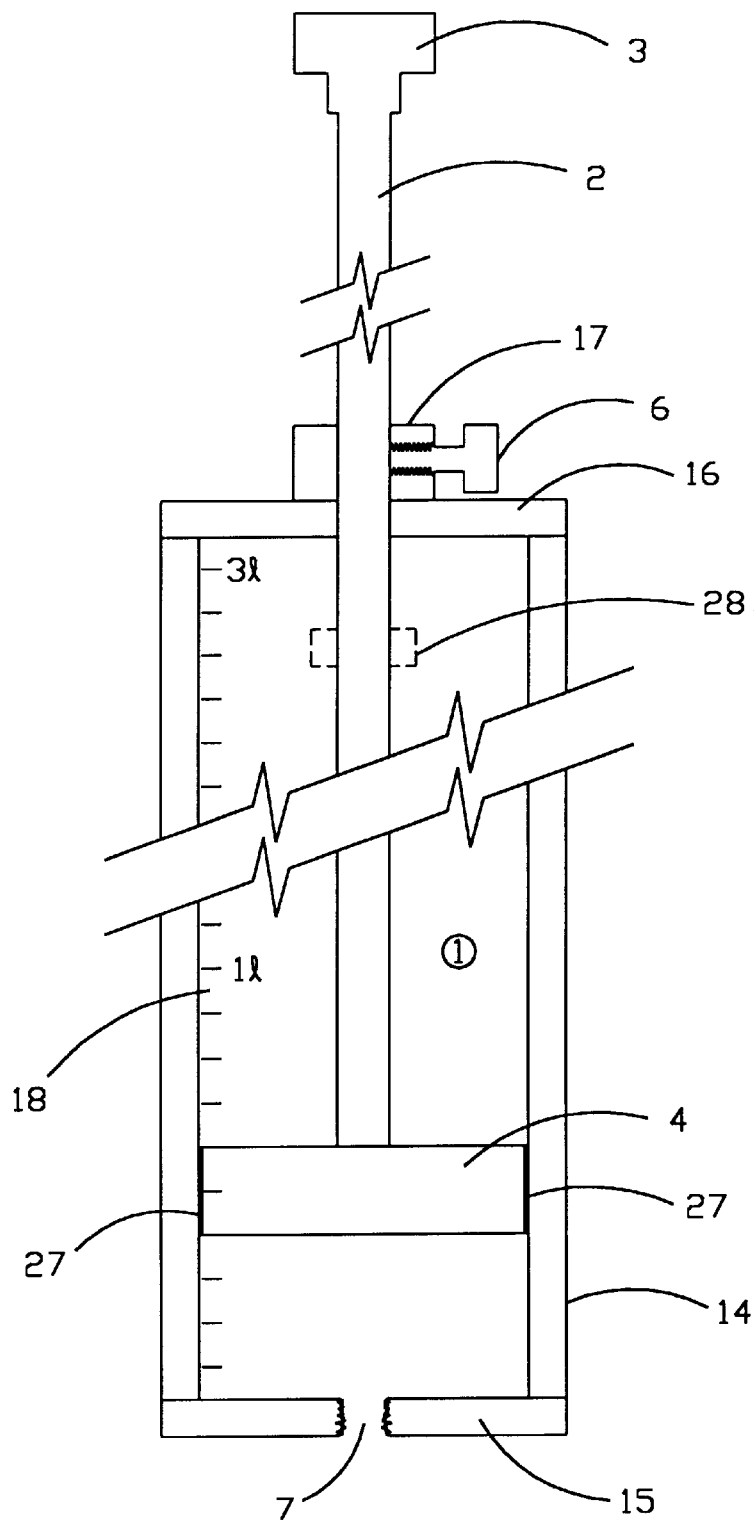
FIG. 3 shows the unmodified collection cylinder.

FIGS. 1 and 3 show the preferred prototype apparatus which consists of a three liter syringe, 1, manufactured by AM Systems under model number CS 3000, incorporating a modified plunger, 4, a stop clamp, 28, axially mounted on the plunger shaft, 2, and a concentric ring, 17, mounted to the upper plate of the syringe, 16, containing a set-clamp, 6. FIG. 2 shows a schematic representation of the apparatus connected to a hemofilter, 21, via the inlet line, 12.

FIG. 1 shows the preferred bottom entry port, 7, on the syringe; however, it should be noted that a side entry port could be used. A side entry port would lead to minor inaccuracies as regards the volumetric measurement of liquid contained within the device. (There are methods to avoid the inaccuracies caused by a side entry device which will be discussed.)

The hemofilter receives the patient's blood, 22, removes waste products and passes purified blood, 23, back to the patient. The waste products (liquids) pass onto the instant invention via the inlet line. (The arrows on the various lines indicate normal flow direction.)

The inlet line, 12, passes through a restrictor, 11, and into a three-way stop cock (or three-way valve), 9. In position "A", the three-way valve will send waste liquid directly to the collection cylinder, 1, via line 8. In position "B" the waste flow to the apparatus is stopped and liquid entrained within the collection cylinder may pass to the proper disposal point, 24. In position "A" liquid flow to the waste disposal point is blocked. The restrictor, 11, is preferably a roller clamp; however, any form of restriction device may be employed. For example, a needle valve, an adjustable hose clamp, or the like.

The inlet line, 12, shown in FIGS. 1 and 2, is medical or surgical hose and connects the waste product outlet of the hemofilter to the three-way stop cock, 9. It should be noted that if a needle valve (not shown) rather than a roller clamp is used as the restrictor, 11, then the inlet line (hose) will comprise of two sections. In a similar manner a piece of surgical hose would serve as lines 8 and 10. The length of these lines, or pieces of hose, is not critical, although line 8 should be short, and would be set by the user to be able to reach the waste disposal bag and the hemofilter.

For simplicity, the instant invention will be described in terms of its first prototype, based on a three-liter syringe, in which the modification to the existing syringe plunger, 4, consisted of a single quarter-inch hole or conduit, 19, with a 0.2 micron hydrophobic filter, 20, inserted within the conduit. The seal system, 17, between the plunger and the walls of the syringe, although necessary, is not a part of the present invention. The prototype continues to utilize the seal system provided by the supplier of the basic syringe.

The health care provider (referred to as provider) obtains settings from the health professional in the form of volume to be removed from the patient on a per time basis. For simplicity and for purposes of discussion, assume that the volume is 1200 milliliters (1.2 liters) per hour. A simple calculation will give the flow rate as 20 milliliters (20 ml) per minute.

The provider would make the necessary initial adjustments. The plunger would be set at the proper volume and the set clamp, 6, would be tightened against the plunger shaft, 2, so that the plunger cannot be moved from the 1.2 liters graduation on the cylinder (syringe). The restrictor would be adjusted to provide an approximate flow of 20 ml/minute. The provider would connect the collection system to the hemofilter, within the dialysis machine, and assure that the drain line is properly terminated.

Assume that proper connections have been made to the hemofilter (and the patient), to the present device, and to the proper disposal point. Further assume that the valve, 9, is in position "B" blocking flow from the hemofilter and that the plunger has been positioned at 1.2 liters (1200 ml) with the set clamp, 6, properly tightened against the plunger shaft, 2. Now allow the valve to be moved to position "A" starting waste liquid flow from the hemofilter and the patient. The liquid passes through the inlet line, 12, through the restrictor, 11, through the valve, 9, through line 8 and into the collection cylinder, 1, via the inlet port, 7. The waste liquid (shown as 25) will displace the entrapped air (shown as 26) within the collection cylinder. The entrapped air will pass through the hydrophobic filter, 20, and into the atmosphere. The waste liquid will continue to flow into the collection cylinder until the liquid comes in contact with the hydrophobic filter at which time all flow stops because of the inherent action of the filter. If the restrictor has been properly set or adjusted, flow will stop within the removal period which, for this example, was one hour. All that remains is to empty the cylinder and restart the cycle.

The provider would move the valve, 9, to position "B" effectively opening the cylinder to the disposal point, 24, while blocking all flow to/from the hemofilter. Air passively enters through the top of the canister (which is open to the atmosphere), passes through the hydrophobic filter or membrane, and fills the space immediately above the waste liquid. The waste liquid is now free to drain off to the disposal point. After the waste liquid has left the container, the provider checks the system and returns the three-way value, 9, to position "A." The removal cycle begins again.

There are two scenarios that could occur which are not normal. First, the flow rate (ml/hour) is too low and the cylinder does not fill within the prescribed time. In this case the provider must adjust the restrictor to increase the flow. Second, the flow may be too high and the cylinder completely fills in less than the prescribed time period. Here the safety function takes over as excess liquid cannot be removed from the hemofilter and/or the patient. The hydrophobic filter stops all flow at the preset maximum volumetric rate per period. (I.e., 1200 ml/hour.) The provider should increase the restriction somewhat (reducing flow) for the next removal period or cycle.

Note the safety feature. The patient is protected from excess fluid removal by the set volume limitation of the apparatus. The problems cause by insufficient liquid removal take slightly longer to develop and the care giver should be able to adjust the rate of removal within a couple of cycles. If the collection device is accidentally knocked over, excess liquid flow will NOT occur, and the preferred device will continue to allow liquid removal until the preset volume is reached. A final safety feature of the device is the "no-spill" aspect of the design. That is, no waste liquid will leave the canister except via the proper disposal point.

The stop clamp, 28, is provided as a convenience to the health provider and is not necessary for proper function of the apparatus. The stop clamp limits the withdrawal position of the plunger.

The set-clamp, 6, assures that the plunger will not move from its required position until the provider desires to reposition it. Further, it has been observed that the patient's hydrostatic (liquid) pressure could exert sufficient pressure on the plunger to move the plunger from its preset position. The set clamp prevents any movement due to body hydrostatic pressure.

If a side entry syringe, rather than a bottom entry syringe, is used a minor modification to the procedure must be made to ensure that the liquid volume within the cylinder is accurate. The cylinder should be partially filled with water (or other similar liquid) and the liquid expelled. The volume of remaining liquid within the cylinder should be noted and added to the removal volume required on a per hour basis. This means that the minor amount of liquid remaining in the cylinder will be incorporated into the removal volume. For purposes of example, assume that this volume is 20 milliliters. Therefore, in setting up the apparatus, the provider would position the plunger at 1220 milliliters and tighten the set clamp at that value. Further, the system would be initially primed with 20 milliliters of liquid in the cylinder. These added steps required by a side entry cylinder led to the development of the preferred apparatus.

Figure 4B:
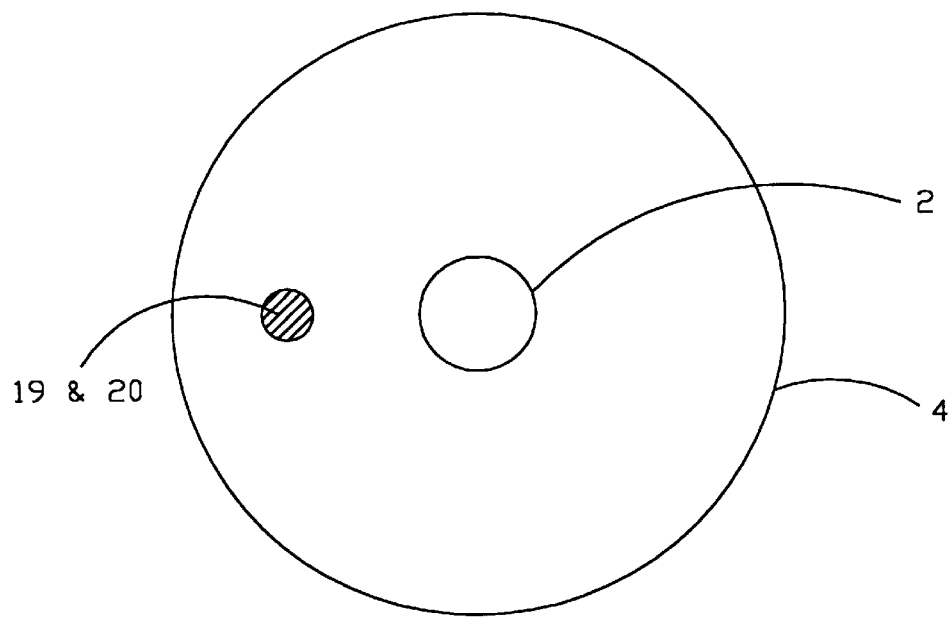
FIG. 4B shows a sectional view of the plunger of FIG. 4A taken at BB.
Figure 4A:
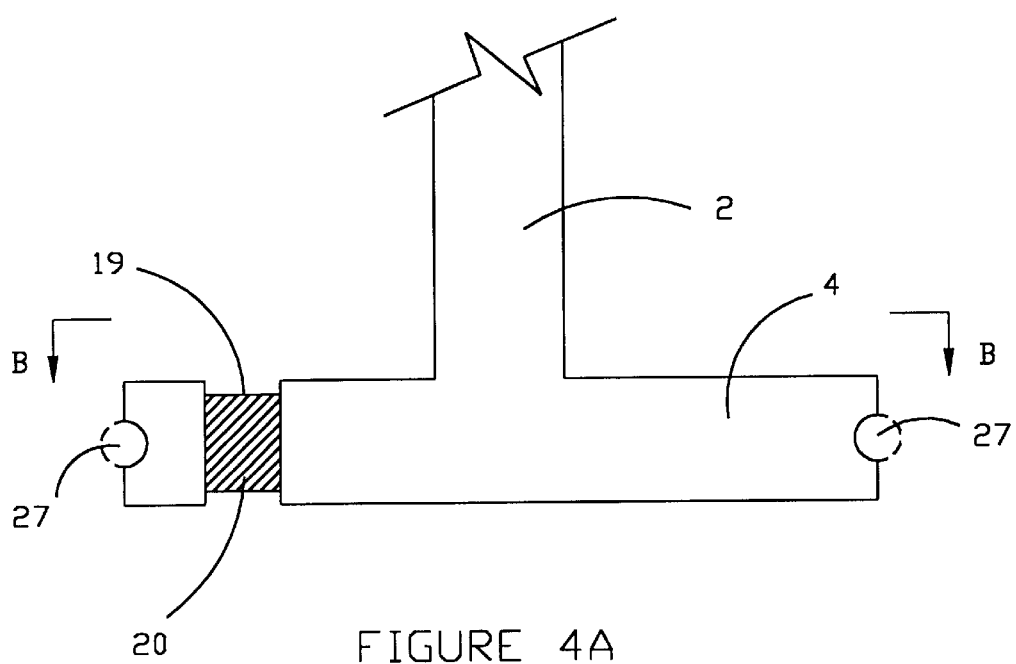
FIG. 4A shows a cross section of the first prototype modified plunger.

FIGS. 4A and 4B show the modified plunger used on the first prototype. A one quarter inch hole forming a quarter inch conduit, 19, is drilled in the plunger. (This conduit could be larger or could consist of a plurality of conduits.) The larger the single conduit (larger area), or a plurality of conduits leading to increase area, the faster the overall hydrophobic filter will recover to allow air flow. The conduit (or plurality of conduits if used) is filled with a 0.2 micron hydrophobic filter, 20. The original seal system, 27, was retained with no modification.

FIGS. 5A through 5D show the preferred modified plunger which consists of a hydrophobic filter cloth stretched out over the bottom surface of the plunger. The preferred modification comes about, as will be explained, due to the possibility of accidental overturning of the collection cylinder and a desire to have the cylinder drain rapidly under gravity. It must be noted that the preferred modified plunger by no way represents a final form of the plunger, because those familiar with the art of manufacturing techniques and designs would easily devise a better method whereby the plunger could be made less complex. The preferred device is explained in keeping with the best mode requirement as contemplated by the inventor.

In testing the first prototype plunger (described above and shown in FIGS. 4A and B), the inventor noted that the time taken to drain the cylinder was inversely proportional to the area of the hydrophobic filter. The inventor noted that the plunger could be forced towards the bottom of the cylinder, by pressing on the plunger knob, 3, but too much pressure would damage the filter or even force the filter out of its conduit, 19.

Figure 5B:
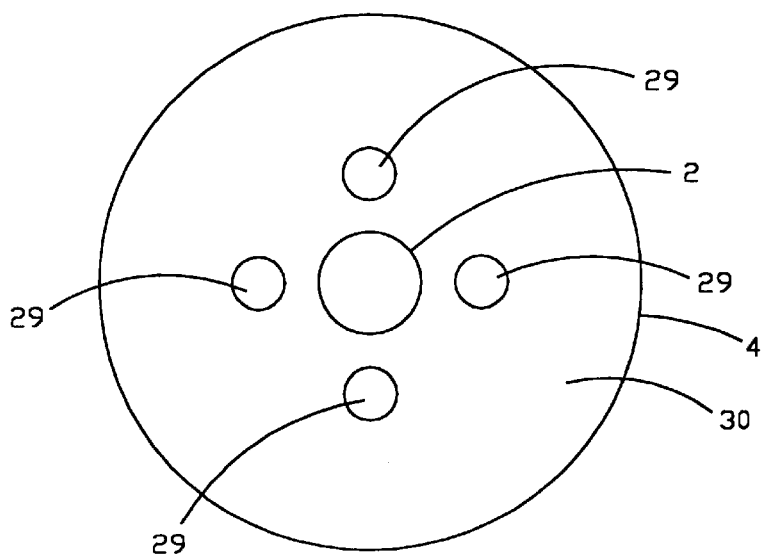
FIG. 5B shows a sectional view of the plunger of FIG. 5A taken at BB.
Figure 5A:
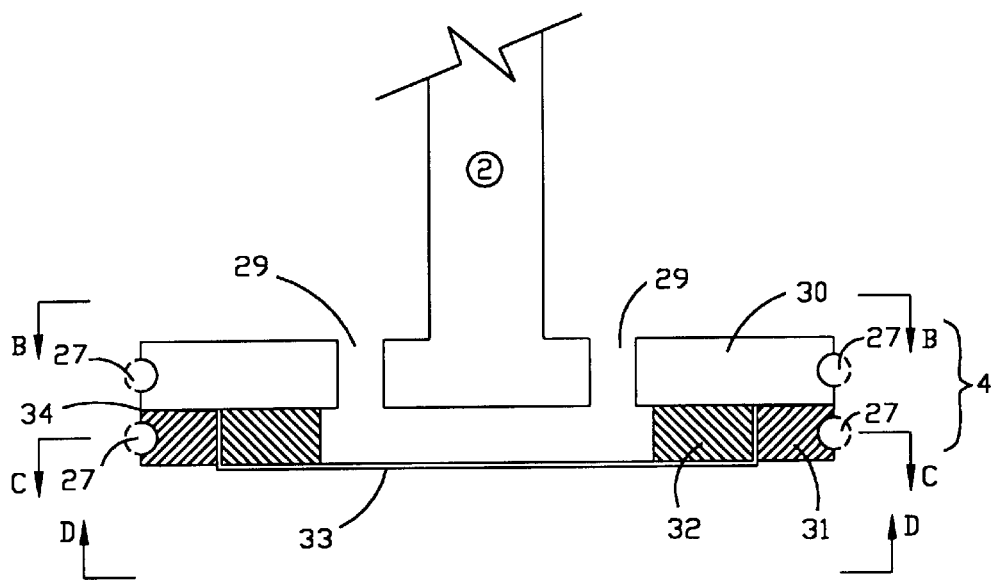
FIG. 5A shows a cross section of the preferred modified plunger.
Figure 5C:
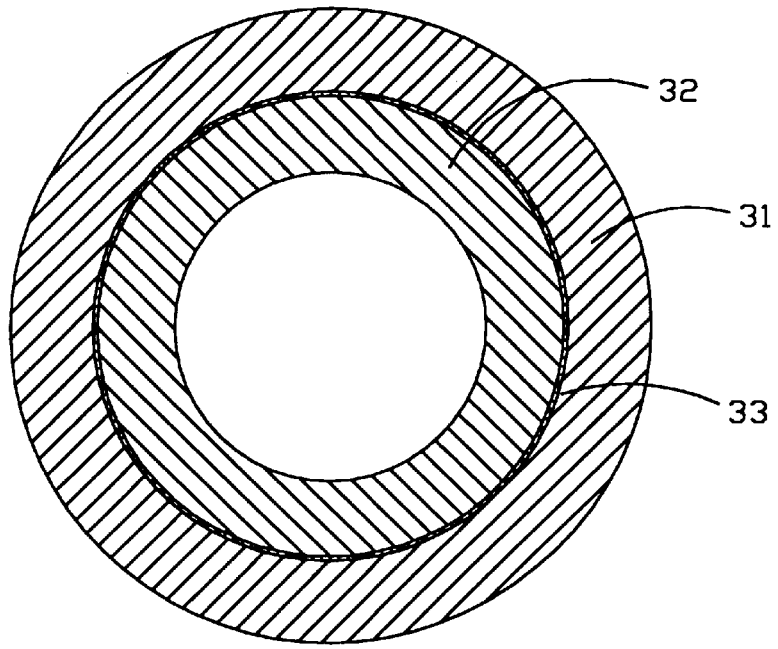
FIG. 5C shows a sectional view of the plunger of FIG. 5A taken at CC.

FIG. 5A shows the best embodiment/mode and the present preferred mode for the modified plunger. The plunger is made from two original plungers, 30 and 31 (supplied by the manufacturer of the syringe/collection canister) held together with screws (not shown). The first plunger, 30, has a series of holes or conduits, 29, bored through the supplied plunger. The second plunger has a single large opening bored through it so that all that remains is a ring, 31, containing the original seal system, 27. A second concentric ring, 32, is manufactured from a convenient plastic material (or even taken from other plungers).

Figure 5D:
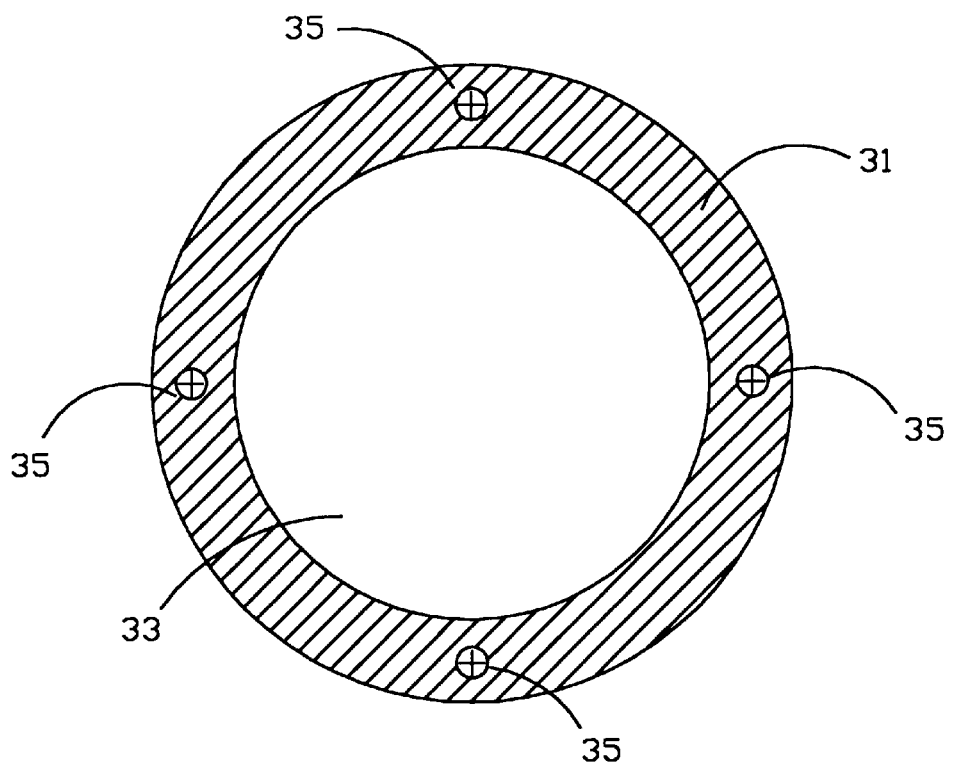
FIG. 5D shows a sectional view of the plunger of FIG. 5A taken at DD.

A sheet of hydrophobic filter material, 33, is stretched over the concentric ring, 32, and held in place by pressing the corresponding ring of the modified plunger, 31, over the filter material. This leaves the filter stretched over the inner concentric ring, held in place by the outer concentric ring, and looking very much like a piece of fabric stretched over a cross-stitch-hoop. The excess filter material extending beyond the outer concentric ring is trimmed. Silicon cement is placed between the upper surface of both the inner and outer concentric rings and the bottom surface of the first modified plunger (surface 34). The outer ring, 31, is affixed to the first plunger, 30, using screws (not shown). The heads, 35, of said retaining screws are shown in FIG. 5D. The original seal system, 27, was retained.

The preferred plunger results in a device that has a large surface area which will allow the container to drain readily. Furthermore, if the canister is accidentally turned over on its side, the hydrophobic filter will not shut off until the waste liquid level is above the highest remaining point of the filter. This point would be located at the junction between the inner and outer ring. In the case of the first prototype, the single filter would shut off as soon as any liquid reached it. A pure of function of position. I.e., if the filter was near the bottom, the filter would shut off early in the cycle; whereas, if the filter happened to be near the top, the filter would shut off later in the cycle.

Experiments with the preferred modified plunger indicate that a full canister will drain under gravity in less than two minutes. Further, it was noted that if the plunger was used to force liquid out of the canister, the hydrophobic filter would eventually fail. It is believed that a person skilled in the art could improve the plunger so that failure of the filter would not occur under back flow conditions. However, it is believed that drainage under gravity, through selective use of the three-way valve, is the best procedure.

There has been disclosed heretofore in the above discussion the best embodiment and best mode of the present invention as presently contemplated and tested. It is to be understood that the examples given and the modifications made may be changed. Slight variations in the attachment of lines, valves and restrictors may be had. For example, the three-way valve may be mounted directly to the inlet/outlet port of the syringe. A restrictor may be incorporated with the three-way valve. Thus, changes may be made to this invention without departing from the spirit of the invention, and, if such modifications are made, they should be construed as being within the spirit of the invention which is to provide an inexpensive safety shut-off waste liquid collection vessel. It is anticipated that this invention could be used in other applications whereby a preset liquid volume should cease flowing after a required time period.

We claim:

1. An adjustable collection canister adapted for collection of waste liquids produced by dialysis equipment comprising:

a cylinder having an inside volume, a bottom, and a top;

a plunger capable of axial movement within said cylinder for adjusting said inside volume thereof and incorporating fluid passage control means allowing gaseous fluids to pass freely through said plunger while limiting the passage of liquids through said plunger;

an entry port located near said bottom of said cylinder and communicating with said inside volume of said cylinder;

means for controlling the movement and position of said plunger within said cylinder;

valve means controlling fluid flow to and from said cylinder;

means for connecting said valve means to said entry port; and means for connecting said valve means to the dialysis equipment.

2. The apparatus of claim 1 wherein said cylinder is graduated in volumetric units.

3. The apparatus of claim 1 further comprising means for regulating the rate of liquid flow from the dialysis equipment into said cylinder.

4. The apparatus of claim 1 further incorporating means for connection to a liquid waste disposal point and wherein said valve means is a three-way valve having a first position and a second position such that when said three-way valve is in said first position liquid flows from the dialysis equipment into said apparatus while liquid flow is blocked to said disposal point and when said valve is in said second position liquid flows from said apparatus to said disposal point while liquid flow is blocked from the dialysis equipment.

5. The apparatus of claim 3 further incorporating means for connection to a liquid waste disposal point and wherein said valve means is a three-way valve having a first adjustable position and a second position such that when said three-way valve is in said first adjustable position liquid flow from the dialysis equipment into said apparatus may be regulated while liquid flow is blocked to said disposal point and when said valve is in said second position liquid flows from said apparatus to said disposal point while liquid flow is blocked from the dialysis equipment.

6. The apparatus of claim 1 further comprising means to prevent axial movement of said plunger within said cylinder.

7. An adjustable collection canister adapted for collection of waste liquids produced by dialysis equipment comprising:

a graduated cylinder having an inside volume, a bottom, and a top;

a plunger capable of axial movement within said cylinder for adjusting said inside volume thereof and incorporating a hydrophobic membrane allowing gaseous fluids to pass freely through said plunger while limiting the passage of liquids through said plunger;

an entry port located near said bottom of said graduated cylinder and communicating with said inside volume of said graduated cylinder;

a plunger shaft passing through said top of said graduated cylinder and connected to said plunger;

valve means controlling fluid flow to and from said graduated cylinder;

means for connecting said valve means to said entry port;

means for connecting said valve means to the dialysis equipment; and means for connecting said valve means to a waste liquid disposal point.

8. The apparatus of claim 7 wherein valve means is a three-way valve having a first position and a second position such that when said three-way valve is in said first position liquid flows from the dialysis equipment into said apparatus while liquid flow is blocked to said disposal point and when said valve is in said second position liquid flows from said apparatus to said disposal point while liquid flow is blocked from the dialysis equipment.

9. The apparatus of claim 7 further comprising means to prevent axial movement of said plunger within said graduated cylinder.

10. An adjustable collection canister adapted for collection of waste liquids produced by dialysis equipment comprising:

a graduated syringe having an inside, a bottom, a top, a plunger, a plunger shaft passing through said top of said graduated syringe connected to said plunger, and an entry port located near the bottom of said graduated syringe communicating with said inside volume of said graduated syringe;

said plunger capable of axial movement within said graduated syringe for adjusting the entrained volume thereof and incorporating a hydrophobic membrane allowing gaseous fluids to pass freely through said plunger while limiting the passage of liquids through said plunger;

valve means controlling fluid flow to and from said graduated syringe;

means for connecting said valve means to said entry port;

means for connecting said valve means to the dialysis equipment; and means for connecting said valve means to a waste liquid disposal point.

11. The apparatus of claim 10 wherein means for connection to the dialysis equipment comprises an appropriate length of hose and further comprises an adjustable clamp positioned on said appropriate length of hose interconnecting the apparatus and the dialysis equipment, said adjustable clamp capable of controlling liquid flow from the dialysis equipment to the apparatus.

12. The apparatus of claim 10 further comprising means to prevent axial movement of said plunger within said graduated syringe.

13. An adjustable collection canister adapted for connection to dialysis equipment for collection of waste liquids produced by dialysis equipment and adapted for connection to a waste liquids disposal point comprising:

a graduated syringe having an inside, a bottom, a top, a plunger, a plunger shaft passing through said top of said graduated syringe connected to said plunger, and an entry port located near said bottom of said graduated syringe communicating with said inside volume of said graduated syringe said plunger capable of axial movement within said graduated syringe for adjusting the entrained volume thereof and incorporating a hydrophobic membrane allowing gaseous fluids to pass freely through said plunger while limiting the passage of liquids through said plunger;

a three-way valve in communication with said entry port;

a first appropriate length of hose connecting said three-way valve to the dialysis equipment;

an adjustable clamp positioned on said first appropriate length of hose, said adjustable clamp capable of controlling liquid flow from the dialysis equipment to said three-way valve;

a second appropriate length of hose connecting said three-way valve with the disposal point;

wherein said three-way valve has a first position and a second position such that when said three-way valve is in said first position liquid flows from the dialysis equipment through said first appropriate length of hose into said entry port while liquid flow is blocked to said disposal point and when said valve is in said second position liquid flows from said entry port through said second appropriate length of hose to said disposal point while liquid flow is blocked from the dialysis equipment; and, means to prevent axial movement of said plunger within said graduated syringe.

* * * * *